| United States Patent [19] | [11] | 4,301,145 |
|---|---|---|
| Cestari | [45] | Nov. 17, 1981 |

[54] ANTISEPTIC SKIN CREAM

[76] Inventor: Joseph E. Cestari, 41 Causeway, Lawrence, N.Y. 11559

[21] Appl. No.: 172,777

[22] Filed: Jul. 28, 1980

[51] Int. Cl.$^3$ ..................... A61K 31/79; A61K 33/18
[52] U.S. Cl. ....................................... 424/80; 424/150
[58] Field of Search .................................. 424/180, 80

[56] References Cited

U.S. PATENT DOCUMENTS 3,150,096  9/1964  Schmidt et al. ............... 424/150 X
3,687,855  8/1972  Halpern ......................... 424/150 X Primary Examiner—Schenkman
Attorney, Agent, or Firm—Bauer & Amer

[57] ABSTRACT

An antiseptic skin cream is taught including a base composition comprising a decolorizing agent, a solvent, a solvent humectant, a preservative, an emulsifier and an ointment base to which is added povidone iodine as the active ingredient. Due to the presence of the decolorizing agent, preferably sodium citrate, the resultant composition has a whitish color.

7 Claims, No Drawings

ANTISEPTIC SKIN CREAM

BACKGROUND OF THE INVENTION

The present invention relates generally to an antiseptic skin cream composition and, more particularly, to such a composition which incorporates polyvinylpyrrolidinone iodine, also known as povidone iodine, as the active ingredient. In the preferred embodiment, the povidone iodine is decolorized by the addition of sodium citrate.

The use of povidone iodine as the active ingredient in an antiseptic skin cream is well known in the prior art. For example, povidone iodine compositions are broadly disclosed in U.S. Pat. Nos. 4,113,857 which issued to B. Shetty on Sept. 12, 1978; 4,088,597 which issued to G. Morlock et al on May 9, 1978; 2,826,532 which issued to W. Hosmer on Mar. 11, 1958; 4,107,407 which issued to A. Cantor et al on Apr. 12, 1977; and 2,776,924 which issued to J. Martin on Jan. 8, 1957. Similarly, the use of povidone iodine as the active ingredient in dermatological cream compositions is disclosed in U.S. Pat. Nos. 4,130,640 which issued on Dec. 19, 1978, to R. Chazan; 4,017,641 which issued to D. Di Giulio on Apr. 12, 1977; 3,671,545 which issued to A. Halpern on June 12, 1972; and 2,876,164 which issued to I. Wershaw on Mar. 3, 1959.

An inherent problem in the use of povidone iodine as an active ingredient in a dermatological preparation is that the natural reddish brown color of the povidone iodine is cosmetically unacceptable. It has been found that demartological creams which are white or clear in color are more cosmetically acceptable as they are less offensive to the user and may "vanish". While other skin preparations have incorporated povidone iodine as the active ingredient, none have consciously attempted to decolorize the povidone iodine to provide a cosmetically acceptable vanishing cream.

Against the foregoing background, it is a primary object of the present invention to provide a povidone iodine based dermatological cream composition which is effective against a variety of bacteria, fungus and viruses.

It is another object of the present invention to provide a povidone iodine based dermatological cream composition which has a cosmetically acceptable appearance.

It is still another object of the present invention to provide a povidone iodine composition wherein decolorization of the povidone iodine is accomplished without any alteration of the cidal effect of the free iodine.

SUMMARY OF THE INVENTION

To the establishment of these objects and advantages, the present invention briefly comprises an antiseptic dermatological cream which includes povidone iodine as its active ingredient. The povidone iodine is combined with a base composition including sodium citrate as a decolorizing agent; a solvent combination selected from the group consisting of cetyl and stearyl alcohols; glcerine as a solvent humectant; a preservative combination selected from the group consisting of propyl and methyl paraben; and sodium lauryl sulfate as an emulsifier. The resultant composition has a white color due to the presence of the sodium citrate.

DESCRIPTION OF THE PREFERRED EMBODIMENTS

The present invention contemplates a dermatological cream composition which includes, as its active ingredient, povidone iodine in an effective cidal amount, preferably between about 5% and about 20% by weight of the base composition. In a particularly preferred embodiment, povidone iodine is included in an amount between about 8% and about 12% by weight of the base composition. Best results have been obtained when the povidone iodine is included in an amount approximately 10% by weight of the base composition. Povidone iodine is a complex of iodine and povidone which is a synthetic polymer consisting essentially of linear 1-vinyl-2-pynolidinone groups (hereafter referred to as polyvinyl pyrrolidone) and is described, for example, in U.S. Pat. No. 2,826,532 which issued to W. Hosmer on Mar. 11, 1958.

The povidone iodine is combined with a base composition consisting of a number of different constituents to achieve the desirable prospects of the resultant composition. For example, it has been found that because of the natural reddish brown color of povidone iodine, a decolorizing agent must be included to render the resultant composition cosmetically acceptable. A particularly preferred decolorizing agent has been found to be sodium citrate in an effective amount between 0.1% and 2% by weight of the base composition. A preferred amount of sodium citrate is between about 0.5% and about 1% by weight of the base composition and a most preferred amount of sodium citrate is about 1% by weight. The sodium citrate selected should contain not less than 99% and not more than 100.5% of $C_6H_5Na_3O_7$ calculated on the anhydrous basis.

In addition to the povidone iodine and decolorizing agent, an emulsifying agent or emulsifier should further be incorporated in an amount between about 2% and about 10% by weight of the base composition. A preferred emulsifying agent is sodium lauryl sulfate in an amount between about 4% and about 6% and most preferably in an amount about 5% of the base composition.

A solvent humectant and emollient, preferably glycerine, is further included in an amount between about 6% and about 20% by weight of the base composition. In a preferred embodiment, glycerine is included in an amount between about 10% and about 15% by weight of the base composition and preferably in an amount equal to about 12% by weight of the base composition. It has been found that in addition to acting as an emollient, the glycerine exhibits certain antiseptic properties.

A combination of alcohols is further included as a solvent. For example, it has been found that cetyl alcohol in an amount between about 2% and about 6% by weight of the base composition and preferably in an amount about 2% by weight renders the composition sufficiently smooth to function as an ointment. Similarly, an amount of stearyl alcohol in an amount between about 2% and about 6% by weight of the base composition and preferably about 3% by weight has been found to act as an emulsifying agent and stabilizer to permit the composition to retain and absorb water in large amounts.

A preservative mixture must be further included to insure that the composition remains stable over a prolonged period of time. To this effect, a combination of propyl paraben and methyl paroben has proven particularly effective. In a preferred embodiment, the propyl paraben and methyl paraben are each included in amounts between about 0.05% and about 0.25% by weight of the base composition and most preferably in an amount about 0.15%. It has been found that the propyl paraben and methyl paraben combination also possesses certain antiseptic properties.

The above constituents are combined in an ointment base in an amount equal 100%. It has been found that white perolatum album is a particularly effective ointment base in an amount between about 65% and about 80% by weight of the base composition.

In addition to the aforementioned ingredients, it is understood that other active ingredients may be incorporated in the composition. For example, triamcinolone, an anti-inflammatory agent, may also be included in effective amounts up to about 1% by weight. It has been found that the dermatological composition with between approximately 0.1% and about 0.5% by weight of the base composition of triamcinolone is particularly effective in reducing inflammation in extensively debraded and infected skin areas. It has further been found that the incorporation of xylocaine in an amount up to about 10% by weight of the base composition has been effective in reducing pain. In particular, the above discussed composition polyiodine complex and triamcinolone including about 5% xylocaine has proven particularly effective when applied to second degree burns.

Although the method of admixture of the above ingredients is not critical, it has been found that it is preferable to initially compound the ingredients of the base composition and then slowly add the povidone iodine to the base composition with mechanical agitation to continue until the povidone iodine color vanishes and the composition becomes white in color.

The resultant dermatological cream possesses bacteriocidal, fungicidal and viricidal properties and, due to its vanishing cream base, can be applied to the skin with no applicable residue. It has been found that the resultant composition is effective in treating the following dermatological conditions: superficial bacterial, viral and fungus infections; sunburn; diaper rash; athlete's foot; jock itch and impetigo; acne; chemical and detergent burns; and infected insect bites. The composition contains approximately 1% free iodine which is equivalent in effectiveness to higher concentrations of free iodine, i.e. between about 2% and about 5% found in fluid or aqueous basis due to the fact that the composition, in cream form, maintains contact with the skin for prolonged periods of time, i.e. between 2 and 6 hours.

The following examples serve to illustrate certain preferred embodiments of the present invention and are not to be construed as limiting the scope of the present invention.

EXAMPLE I

In order to illustrate the dermatological composition of the present invention, a base composition consisting of the following was prepared:

| | % by weight |
|---|---|
| sodium citrate | 1% |
| cetyl alcohol | 2% |
| stearyl alcohol | 3% |
| glycerine | 12% |
| sodium lauryl sulfate | 5% |
| propyl paraben | 0.15% |
| methyl paraben | 0.15% |
| petrolatum album | balance to 100% |

To the above admixed base composition was added the povidone iodine in an amount of 10% by weight of the base composition under constant agitation which continued until the reddish brown color of the povidone iodine disappeared.

The resultant composition was then applied topically to a patient having an acute jock itch infection three times per day for 72 hours after which a complete remission was observed.

EXAMPLE II

The composition of Example I was topically applied to a subject who had severely inflamed impetigo on both arms and legs. After application for 48 hours, remission was observed and complete healing occurred in seven days.

EXAMPLE III

A composition similar to the composition of Example I was prepared containing, however, 0.5% of sodium citrate. The composition, which was decolorized, was applied topically to a patient who had recently received 25 stitches from a laceration which had become infected. No systemic antibiotics were used. Remission occurred within 24 hours and complete healing occurred within ten days with minor scarring.

EXAMPLE IV

A composition similar to the composition of Example I was prepared containing, however, 0.7% sodium citrate. The resultant composition was topically applied to a subject having infected acne twice per day for one week after which a 50% remission had occurred.

EXAMPLE V

The composition of Example IV was prepared and topically applied to a patient having an infected and inflamed rash at a rate of four times per day. Relief occurred after three days and complete healing occurred in six days.

EXAMPLE VI

The composition of Example IV was prepared and topically applied to a patient having a herpes infection on approximately 75% of his scalp. The composition was applied every four hours for 24 hours at which time healing began. After seven days, 80% of the infection had healed.

EXAMPLE VII

A composition similar to the composition of Example I was prepared containing, however, 20% povidone iodine and 2% sodium citrate. The resultant composition was a brownish red in color indicating that complete decolorization had not occurred.

EXAMPLE VIII

A composition similar to the composition of Example I was prepared containing, however, 0.1% triamcinolone and the resultant composition was topically applied to a patient having debraded skin due to a severe chemical burn. Improvement in reduced inflammation was observed within 24 hours and an 80% remission was seen in 48 hours after commencement of treatment.

EXAMPLE IX

A composition similar to the composition of Example VIII was prepared containing, however, 0.5% triamcinolone and the resultant composition was topically applied to an infant having a severely infected diaper rash. Improvement was observed within 24 hours and noticeable clearing of the skin occurred within 72 hours. The composition of Example I was then applied for an additional four days at which time the skin had totally cleared up.

EXAMPLE X

A composition similar to the composition of Example IV was prepared additionally containing 5% xylocaine. The resultant composition was applied topically to a patient having second degree burns on both arms. The composition was applied every four hours for two days followed by application of the composition of Example IV for an additional three days after which time 75% of the burned tissue had healed with no noticeable infection.

Although the foregoing examples illustrate certain specific compositions, it will be appreciated that the teaching of this application encompass broader and different combinations than recited herein. Accordingly, the present invention should be limited only by the true scope of the appended claims.

What is claimed is:

1. An antiseptic dermatological cream composition comprising:
   povidone iodine as an active cidal agent in an amount between about 5% and about 20% by weight of the total composition;
   sodium citrate as a decolorizing agent in an amount between about 0.2% and about 2% by weight of said composition;
   glycerine in an amount between about 10% and about 15% by weight of said composition;
   a solvent selected from the group consisting of stearyl alcohol and cetyl alcohol in an amount between about 4% and about 12% by weight of said composition;
   a perservative selected from the group consisting of propyl paraben and methyl paraben in an amount between about 0.1% and about 0.5% by weight of said composition;
   sodium lauryl sulfate as an emulsifier in an amount between about 2% and about 10% by weight of said composition; and
   an ointment petroleum base in an amount up to about 85% by weight of said composition.

2. The composition of claim 1 wherein said ointment base is white petrolatum.

3. The composition of claim 1 further including xylocaine in an amount up to about 10% by weight of the composition.

4. The composition of claim 1 further including triamcinolone in an amount between about 0.1% and about 0.5% by weight of the composition.

5. An antiseptic dermatological cream composition comprising:
   povidone iodine as an active cidal agent in an amount between about 8% and about 12% by weight of said composition;
   sodium citrate as a decolorizing agent in an amount between about 0.5% and about 1% by weight of the composition;
   glycerine in an amount between about 10% and about 15% by weight of the composition;
   at least one solvent selected from the group consisting of stearyl alcohol and cetyl alcohol in an amount between about 4% and about 5% by weight of the composition;
   at least one perservative selected from the group consisting of propyl paraben and methyl paraben in an amount between about 0.1% and about 0.5% by weight of the composition;
   sodium lauryl sulfate in an amount between about 4% and about 6% by weight of the composition;
   and a white petrolatum base in an amount between about 65% and about 80% by weight of the composition.

6. The composition of claim 5 further including triamcinolone in an effective amount.

7. The composition of claim 5 further including xylocaine in an effective amount.

* * * * *